United States Patent [19]

Udd et al.

[11] Patent Number: 4,471,659

[45] Date of Patent: Sep. 18, 1984

[54] OPTICAL VIBRATION SENSOR

[75] Inventors: Eric Udd; Richard F. Cahill, both of Orange County, Calif.

[73] Assignee: McDonnell Douglas Corporation, Long Beach, Calif.

[21] Appl. No.: 509,942

[22] Filed: Jul. 1, 1983

[51] Int. Cl.³ .................. G01N 29/00; G01H 9/00
[52] U.S. Cl. ..................... 73/655; 73/657; 350/358
[58] Field of Search ............... 73/655, 657; 367/149; 350/358

[56] References Cited

U.S. PATENT DOCUMENTS

| | | | |
|---|---|---|---|
| 4,321,464 | 3/1982 | Miller | 73/655 |
| 4,422,167 | 12/1983 | Shajenko | 367/149 |
| 4,450,541 | 5/1984 | Tietjen | 367/149 |

Primary Examiner—Howard A. Birmiel
Attorney, Agent, or Firm—George W. Finch; John P. Scholl; Donald L. Royer

[57] ABSTRACT

A vibration sensor is formed by coupling the vibration to be sensed to change the positional relationship between grating means and light beams so that the resultant variations in light intensity of the beams beyond the grating means vary with a function of the sine and cosine of the positional change. This allows the detection of the vibration over a wide range of frequencies and amplitudes.

20 Claims, 8 Drawing Figures

4,471,659

OPTICAL VIBRATION SENSOR

BACKGROUND OF THE INVENTION

Light sources, in combination with gratings, have been used as means for detecting acoustic waves, angular positions and environmental changes. However, such devices either have a limited dynamic range or low sensitivity. This is because to achieve high sensitivity, grating lines must have been closely spaced so that small motions result in large intensity modulation. However, to achieve wide dynamic range without saturation or fold-over, the grating spacing has had to be quite wide, resulting in low sensitivity.

BRIEF DESCRIPTION OF THE PRESENT INVENTION

In the present invention, light beams and a grating movable with respect to the beams are used to produce sine and cosine signals simultaneously through the light modulation action of the grating so that the lines of the grating can be very closely spaced, for example 25 microns between line pairs, to achieve high sensitivity, yet because of the quadrature detection scheme the dynamic range can be sensed over multiple grating lines, thus achieving wide dynamic range and high sensitivity at the same time.

Therefore, it is an object of the present invention to provide a grating type vibration sensor having a wide dynamic range and high sensitivity.

Another object is to provide a sensor which can be constructed relatively economically while being capable of withstanding the rigorous environments which seismic and undersea detectors are forced to withstand.

Another object is to provide a vibration sensor which is easily calibrated.

Another object is to provide a vibration detector which can use readily available components.

These and other objects and advantages of the present invention will become apparent to those skilled in the art after considering the following detailed specification along with the accompanying drawings wherein:

DETAILED DESCRIPTION OF THE SHOWN EMBODIMENTS

Figure 1:
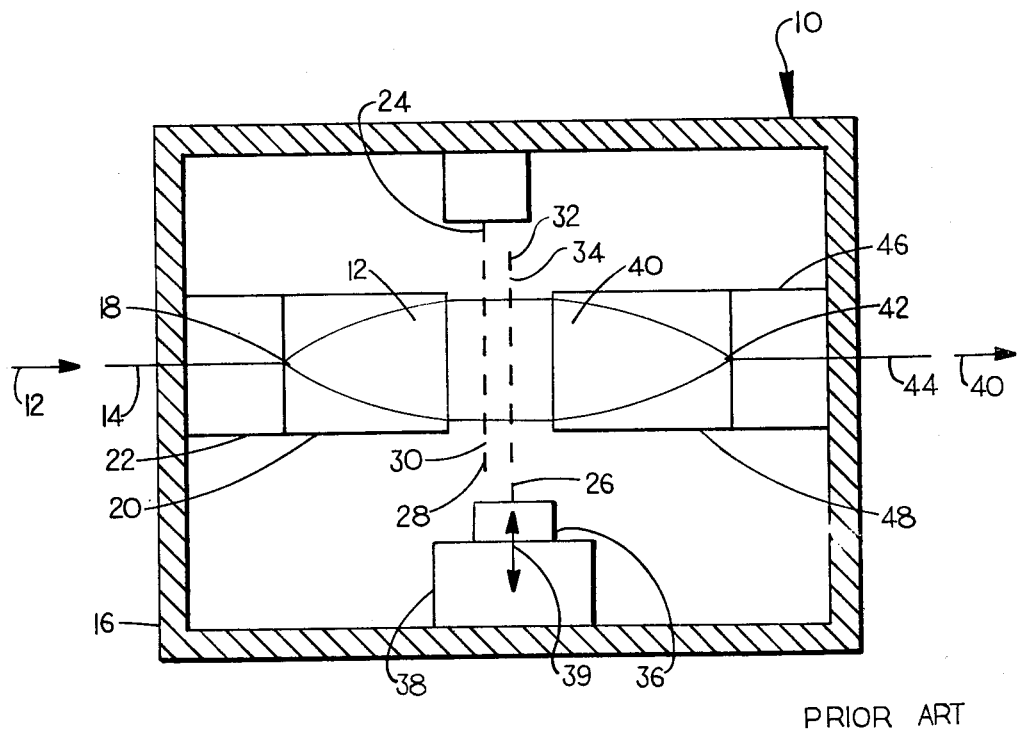
FIG. 1 is diagrammatic representation of a prior art vibration sensor utilizing gratings and light intensity.

Referring to the drawings, more particularly by reference numbers, number 10 in FIG. 1 refers to a prior art sensor for detecting acoustic waves angular positions or environmental changes. In the sensor 10, an input light beam 12 is transmitted through an optical fiber 14 within the body 16 of the sensor 10. The output end 18 of the fiber 14 is held in position adjacent a quarter pitch graded index lens 20 by means of a suitable ferrule 22. The graded index lens 20 expands the input light beam 12 and projects it with parrallel rays through a grating 24 fixedly mounted to the body 16. The fixed grating 24 as well as a floating grating 26 have parallel strips 28 and 30, and 32 and 34 which are alternately opaque and transparent. Since the gratings 24 and 26 are constrained to remain parallel, the opaque strips 28 and 32 interupt the light of the beam 12 so that at one relative position of the strips 28 and 32 essentially all of the light is blocked from passage therethrough, whereas at another relative position about half of the light is able to pass therethrough.

Figure 2:
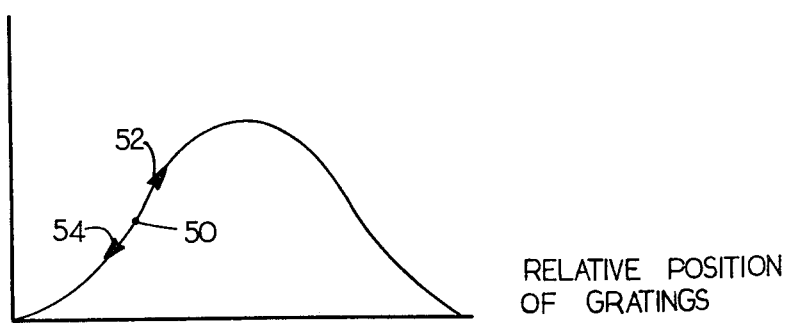
FIG. 2 is a diagram of output intensity versus relative grating movement for the prior art sensor shown in FIG. 1.

The floating grating 26 preferably is mounted in combination with a mass 36 on a spring 38. The spring 38 is designed to allow relative movement between the grating 26 and the body 16 along a predetermined line 39 so that movement of the body 16, within the design range of the sensor 10, causes the fixed grating 24 to move with the body 16 while the floating grating 26 remains relatively fixed in space in the predetermined direction 39 due to the inertia of the mass 36. Therefore, the movements applied to the sensor 10 convert the beam 12 into a modulated light beam 40 which is recollimated onto the input end 42 of an output fiber 44 held in place by a ferrule 46 by a second quarter pitch graded index lens 48. The intensity of the output beam 40 versus the relative positions of the gratings 24 and 26 is shown in FIG. 2.

In order to maximize sensitivity and assure linearity, the "at rest" relative positioning of the fixed grating 24 and the floating grating 26 are placed in relative positions where about one quarter of the intensity of the input beam 12 appears on the output beam 40. This is shown as point 50. Thereafter, raising or lowering of the intensity of the output beam 40 as shown by the arrows 52 and 54 indicates a change in relative position between the fixed and floating gratings 24 and 26. In many applications, the sensor 10 is unsatisfactory because there must be a major tradeoff between dynamic range and high sensitivity in its design. That is, in order to achieve high sensitivity, the opaque and transparent grating strips 28 and 30, and 32 and 34 should be as closely spaced as possible so that small relative motions between the gratings 24 and 26 result in large intensity changes. However, to achieve wide dynamic range without saturation or foldover, the spacing of the strips 28 and 30, and 32 and 34 should be quite wide.

Figure 3:
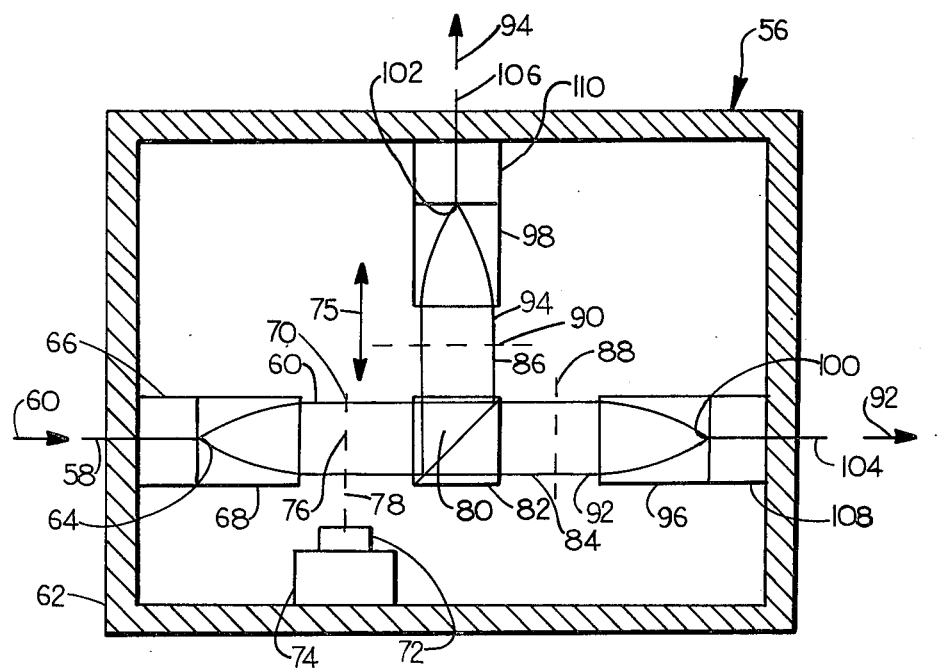
FIG. 3 is a vibration sensor employing gratings to modulate light intensity constructed according to the present invention.

In the present sensor 56, quadrature detection is used to overcome these disadvantages of the prior art sensor 10. As shown in FIG. 3, the sensor 56 includes an input fiber 58 which transmits an input light beam 60 within the body 62 of the sensor 56. The output end 64 of the fiber 58 is held by a ferrule 66 adjacent a quarter pitch graded index lens 68 which expands the beam 60 for projection onto a floating grating 70. Like in sensor 10, the floating grating 70 with a mass 72 is mounted to the body 62 by means of a spring 74 designed to allow relative movement therebetween only in a predetermined direction shown by arrow 75. Therefore, the grating 70 tends to remain stationary in space when the body 62 is moved in the predetermined direction.

Figure 4:
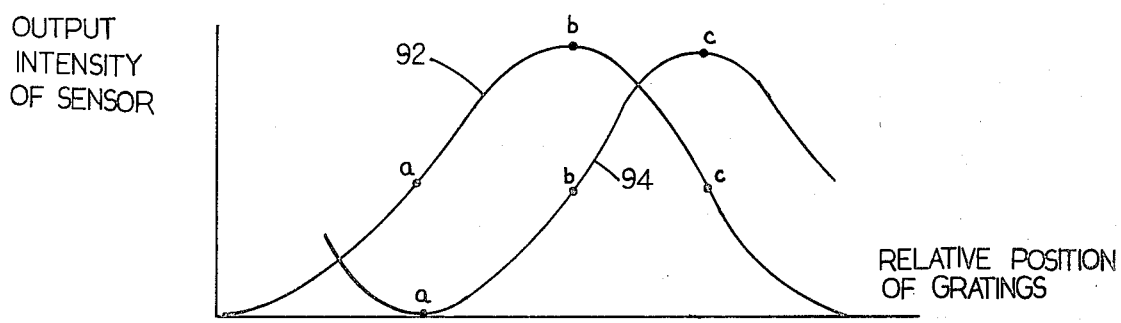
FIG. 4 is a diagram of output intensity versus relative grating movement for the sensor of FIG. 3.

The grating 70 can include very finely spaced opaque and transparent strips 76 and 78 which create a beam 80 having a pattern of parallel dark and light stripes whose vertical position in the beam 80, in the orientation of FIG. 3, is determined by the relative positioning of the grating 70 with respect to the body 62. The beam 80 is projected onto a beamsplitter 82 which projects relatively equal beam portions 84 and 86 thereof through gratings 88 and 90 respectively which have the same grating pattern and orientation as the stripes of the portions 84 and 86, but which are fixedly positioned to the body 62, essentially 90° out of phase with each other. The resultant beams 92 and 94 which pass through the gratings 88 and 90 are recollimated by quarter pitch graded index lenses 96 and 98 respectively onto the input ends 100 and 102 of sine and cosine output fibers 104 and 106 respectively, which are held against the graded index lens 96 and 98 by ferrules 108 and 110. The intensity of the beams 92 and 94 with respect to the relative positions of the floating grating 70 and the fixed gratings 88 and 90 is shown in FIG. 4. The two output signals, 92 and 94, correspond to the sine and cosine of the phase position of the grating 70 with respect to the positions of the gratings 88 and 90. This has two advantages. A continuous output signal can be produced from the light beams 92 and 94 which does not fade as the sine and cosine of the phase position go through zero because it does not occur simultaneously. Therefore, the sine and cosine of the phase position can be used to determine the instantaneous relative position of the grating 70, and tracking may be performed through multiple pairs of grating strips 76 and 78.

Figure 5:
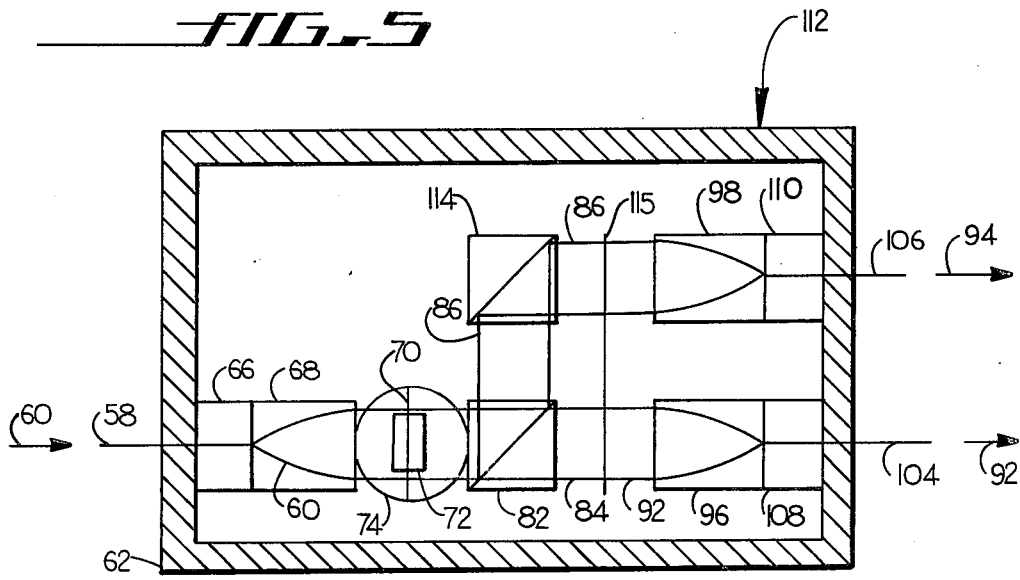
FIG. 5 is a modified form of the sensor of FIG. 3.
Figure 6:
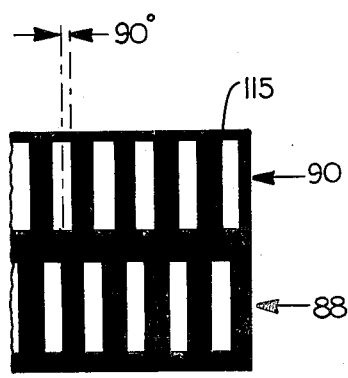
FIG. 6 is an enlarged detailed view of a grating for use in the embodiment of the invention shown in FIG. 5.

However, under certain circumstances it is difficult to properly position and mount the components of the sensor 56 to prevent their relative movement out of quadrature with temperature, age and other environmental conditions. A partial solution to this problem is shown in FIGS. 5 and 6 wherein the sensor 56 is modified into sensor 112 by providing a prism 114 to bend the beam 86 parallel to the beam 84. Therefore, the gratings 88 and 90 can be formed on the same plate 115 so that the 90° out of phase orientation is fixed during the manufacturing process of the plate 115 and relative positioning within the body 62 is more easily controlled. However, there still exists the problem of maintaining the alignment of the graded index lens 96 and 98 as well as the additional complexity of positioning two separate gratings 88 and 90 on the same plate 115.

Figure 7:
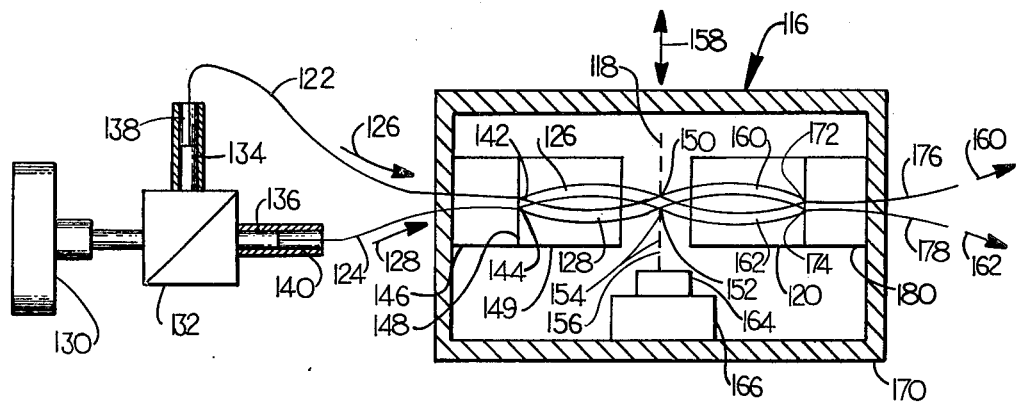
FIG. 7 is a diagrammatic, partial cross-sectional view of another modified form of the present sensor.

Therefore, the sensor 116 reverts to a single floating grating 118 as well as a single output lens 120 as was found in the prior art sensor 10. In sensor 116, shown in FIG. 7, two input fibers 122 and 124 are employed with light beams 126 and 128 passing therethrough from a light source such as a laser diode 130 whose output is split by a beamsplitter 132 and coupled into the fibers 122 and 24 by suitable collimating lens 134 and 136 and ferrules 138 and 140. The output ends 142 and 144 of the fibers 122 and 124 are held together closely by means of a ferrule 146 adjacent the front surface 148 of an input half pitch graded index lens 149 which is capable of focusing the beams 126 and 128 into spots 150 and 152 on the grating 118. In the orientation of FIG. 7, the initial vertical spacing of the ends 142 and 144 usually is chosen to be equal or slightly larger than a 90° phase shift as determined by the vertical spacing between horizontal opaque strips 154 defining the transparent strips 156 of the grating 118. The vertical spacing may be larger if other than adjacent strips 154 and 156 are to be used at the same time. The horizontal spacing of the ends 142 and 144 is not critical but should be close to reduce the chances of error from undesired rotation of the grating 118.

The grating 118 is mounted for relative movement in the directions of the arrow 158 perpendicular to the strips 154 and 156 so that the intensity of the resulant sine and cosine output beams 160 and 162 depends upon the relative positioning of the grating 118 with respect to the ends 142 and 144. Like before, the grating 118 is mounted with a mass 164 on a spring 166 so that it tends to remain stationary as the body 170 of the sensor 116 is moved by vibratory inputs. The beams 160 and 162 are focused (reimaged) by the half pitch graded index lens 120 onto the input ends 172 and 174 of sine and cosine output fibers 176 and 178 which correspond to output fibers 104 and 106 in FIGS. 3 and 5. The ends 172 and 174 are held by a suitable ferrule 180. By having the spacing between the ends 142 and 144 slightly more than the spacing of the opaque strips 154 on the grating 118 enables easy calibration of the sensor 116. For calibration, the lens 149 and 120 can be moved with respect to each other until the beams 126 and 128 produce maximum intensities of beams 160 and 162. Thereafter, the grating 118 is inserted and the ferrule 146 holding the ends 142 and 144 is rotated until perfect quadrature is obtained at which point, the rotation thereof is fixed. Then the ferrule 180 is rotated to match the rotation of the ferrule 146 to regain full intensity. If the initial spacing between the ends 142 and 144 is too small, the lens 149 can be chosen to magnify the image to increase separation. Conversely, the lens 149 can be chosen to reduce the image size if the ends 142 and 144 are too far apart.

Figure 8:
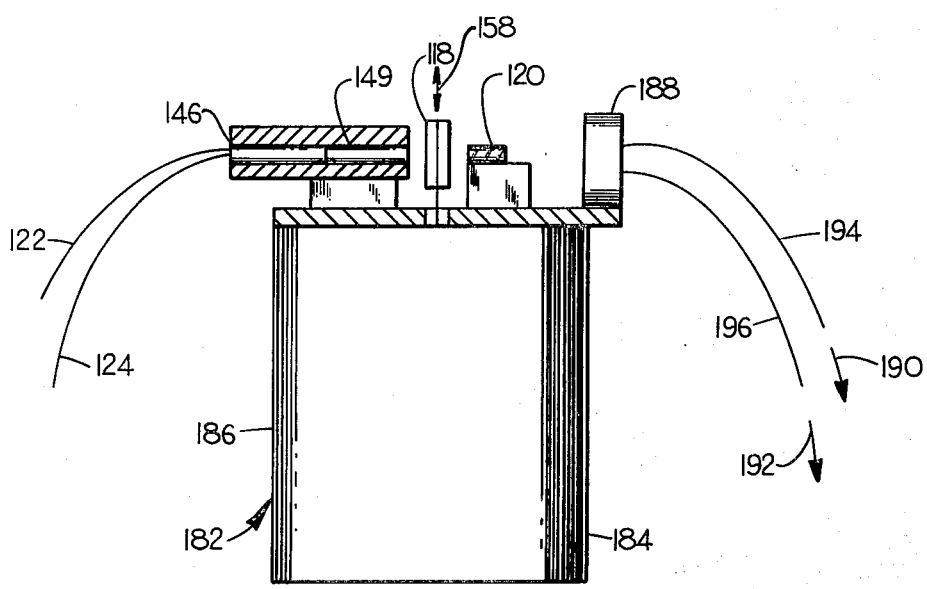
FIG. 8 is a side-elevational view of a seismic sensor constructed by combining mechanical components of a conventional seismometer with the sensor shown in FIG. 7.

A typical embodiment 182 of the invention shown in FIG. 7 is shown in FIG. 8 wherein the grating 118 is mounted to the movable portion of a conventional seismometer 184 with the input lens 149 and output lens 120 being solidly mounted to the case 186 of the seismometer 184. Seismic inputs to the seismometer 184 cause relative motion of the grating 118 as before and result in modulation of the beams 126 and 128 passing therethrough. These beams are imaged by the lens 120 onto a split inline detector 188 which converts the intensity thereof into electrical signals 190 and 192 on signal lines 194 and 196. The signals 190 and 192 are transmitted to suitable electric processing means for quadrature detection of the seismic signal.

Thus there has been shown and described novel vibration sensors which fulfill all the objects and advantages sought therefor. Many changes, modifications, variations, and other uses and applications of the subject invention will however become apparent to those skilled in the art after considering this specification and the accompanying drawings. All such changes, modifications, alterations and other uses and applications which do not depart from the spirit and scope of the invention are deemed to be covered by the invention which is limited only by the claims which follow.

What is claimed is:

1. A vibration sensor including:
   a body to which the vibrations to be sensed are applied;

a first grating having:
   parallel lines aligned on a plane thereon which extend in a first predetermined direction; and
   a predetermined mass;
support means connecting said first grating to said body for movement generally perpendicular to said parallel lines;
light source means to produce a first light beam; and
means to direct said first light beam to said first grating for modulation into first and second output signals which vary in intensity with the vibrations being sensed and are 90° out of phase.

2. The vibration sensor as defined in claim 1 wherein said means to direct said first light beam to said first grating for modulation into first and second output signals include:
   means to produce a second light beam;
   a first optical fiber having input and output ends;
   means to couple said first light beam into said input end of said first optical fiber;
   a second optical fiber having input and output ends;
   means to couple said second light beam into said input end of said second optical fiber, said first and second light beams projecting out of said output ends of said first and second optical fibers respectively and said output ends of said first and second optical fibers being positioned a first predetermined distance apart; and
   lens means to image said first and second light beams projecting out of said output ends of said first and second optical fibers onto said first grating to produce said first and second output signals.

3. The vibration sensor as defined in claim 2 wherein said parallel lines on said first grating are alternate opaque and transparent lines of a predetermined width, said output ends of said first and second optical fibers being spaced apart at least one half said predetermined width in the direction of said predetermined width.

4. The vibration sensor as defined in claim 3 wherein said lens means include:
   a first graded index lens having an odd number of half pitches.

5. The vibration sensor as defined in claim 4 further including:
   a second lens positioned opposite said first grating from said first graded index lens to reimage said first and second light beams into said first and second output signals.

6. The vibration sensor as defined in claim 4 further including:
   a dual detector; and
   a second lens positioned opposite said first grating from said first graded index lens to reimage said first and second light beams into said first and second output signals on said dual detector.

7. The vibration sensor as defined in claim 4 further including:
   a third optical fiber having an input end;
   a fourth optical fiber having an input end; and
   a second lens positioned opposite said first grating from said first graded index lens to reimage said first and second light beams into said first and second output signals on said input ends of said third and fourth optical fibers respectively.

8. The vibration sensor as defined in claim 7 wherein said light source is a laser diode.

9. The vibration sensor as defined in claim 3 wherein said first and second optical fibers are positioned in a ferrule perpendicular to said first grating.

10. The vibration sensor as defined in claim 3 wherein said support means include a seismometer.

11. The vibration sensor as defined in claim 3 wherein said means to produce a second light beam include:
   a beamsplitter positioned to split said second light beam out of said first light beam.

12. The vibration sensor as defined in claim 1 wherein said means to direct said first light beam to said first grating for modulation into first and second output signals include:
   a first optical fiber having:
      an input end positioned to receive said first light beam from said light source means; and
      an output end;
   a first lens having an odd number of quarter pitches positioned to expand said first light beam into parallel rays and project said expanded first light beam through said first grating to form a grated first light beam;
   a second grating similar to said first grating fixed to said body;
   a third grating similar to said first grating fixed to said body positioned 90° out of phase with said second grating; and
   means to split said grated first light beam into second and third light beams, project said second light beam through said second grating, and project said third light beam through said third grating.

13. The vibration sensor as defined in claim 12 wherein said means to split said grated first light beam into second and third light beams, project said second light beam through said second grating, and project said third light beam through said third grating include:
   a beamsplitter cube.

14. The vibration sensor as defined in claim 12 wherein said means to direct said first light beam to said first grating for modulation into first and second output signals further include:
   a second optical fiber having an input end;
   a third optical fiber having an input end;
   a second lens having an odd number of quarter pitches positioned to focus said grated second beam of light into said input end of said second optical fiber to form said first output signal; and
   a third lens having an odd number of quarter pitches positioned to focus said grated third beam of light into said input end of said third optical fiber to form said second output signal.

15. The vibration sensor as defined in claim 14 wherein said means to direct said first light beam to said first grating for modulation into first and second output signals include:
   a planar plate fixedly connected to said body on which both said second and third gratings are positioned, and wherein said means to split said grated first light beam into second and third light beams, project said second light beam through said second grating, and project said third light beam through said third grating projects said second and third light beams parallel to each other.

16. The vibration sensor as defined in claim 15 wherein said means to split said grated first light beam into second and third light beams, project said second light beam through said second grating, and project said third light beam through said third grating include:

a beamsplitter cube positioned to split said grated first light beam into second and third light beams; and a mirror positioned to reflect said second light beam parallel to said third light beam.

17. The vibration sensor as defined in claim 16 wherein said second grating includes parallel lines and said third grating includes parallel lines parallel to said parallel grating lines of said second grating.

18. The vibration sensor as defined in claim 14 wherein said first, second and third lens are graded index lens.

19. The vibration sensor as defined in claim 13 wherein said second and third gratings are positioned at right angles to each other.

20. The vibration sensor as defined in claim 19 wherein said parallel lines on said first, second, and third gratings are alternate opaque and transparent lines of a predetermined width.

* * * * *